United States Patent
Shuttleworth et al.

(10) Patent No.: US 9,266,879 B2
(45) Date of Patent: Feb. 23, 2016

(54) NAPHTHRIDINE DERIVATIVES AS PI3K INHIBITORS FOR THE TREATMENT OF CANCER AND IMMUNE-INFLAMMATORY DISEASE

(75) Inventors: Stephen Joseph Shuttleworth, Hampshire (GB); Franck Alexandre Silva, Hampshire (GB)

(73) Assignee: Karus Therapeutic Limited, Hampshire (GB)

( * ) Notice: Subject to any disclaimer, the term of this patent is extended or adjusted under 35 U.S.C. 154(b) by 232 days.

(21) Appl. No.: 13/643,210

(22) PCT Filed: Apr. 26, 2011

(86) PCT No.: PCT/GB2011/050824
§ 371 (c)(1),
(2), (4) Date: Jan. 7, 2013

(87) PCT Pub. No.: WO2011/135351
PCT Pub. Date: Nov. 3, 2011

(65) Prior Publication Data
US 2013/0109688 A1     May 2, 2013

(30) Foreign Application Priority Data
Apr. 30, 2010 (GB) .................................. 1007347.6

(51) Int. Cl.
*C07D 471/04* (2006.01)
(52) U.S. Cl.
CPC .................................... *C07D 471/04* (2013.01)
(58) Field of Classification Search
None
See application file for complete search history.

(56) References Cited

U.S. PATENT DOCUMENTS

| | | |
|---|---|---|
| 4,017,500 A | 4/1977 | Mayer |
| 2011/0201608 A1 | 8/2011 | Hoffmann et al. |

FOREIGN PATENT DOCUMENTS

| | | |
|---|---|---|
| EP | 1724267 A1 | 11/2006 |
| WO | WO-2008/150827 A1 | 12/2008 |
| WO | WO-2010/015520 A1 | 2/2010 |
| WO | WO-2010/037765 A2 | 4/2010 |

OTHER PUBLICATIONS

"Novel cAMP PDE III Inhibitors: 1,6-Naphthyridin-2(1H)-ones" by Alvarez-Rua et al., New J. Chem. 28, 700-07 (2004).*
CAS Registry Nos. 1214438-02-4 and 1214393-37-9 (Mar. 25, 2010).*
D. A. Kovalskiy et al., "Synthesis of 7-(3-Piperidyl)[1,6] Naphthyridine and 7-(4-Piperidyl) [I,6]Naphthyridine", *Chemistry of Heterocyclic Compounds*, 45(9): 1053-1057, Nov. 24, 2009.
Erik L. Meredith et al., "Identification of Orally Available Naphthyridine Protein Kinase D Inhibitors", *Journal of Medical Chemistry*, 53(15): 5400-5421, Aug. 12, 2010.
Baldev Singh et al., "Novel cAMP PDE III Inhibitors: 1,6-Naphthyridin-2(18)-ones", *Journal of Medical Chemistry*, American Chemical Society, 35(26): 5858-4865, Jan. 1, 1992, New York.
Database Chemcats [Online], *Chemical Abstracts Service*, Apr. 22, 2011, Columbus, Ohio.

* cited by examiner

*Primary Examiner* — Theodore R West
(74) *Attorney, Agent, or Firm* — Goodwin Procter LLP

(57) ABSTRACT

Compounds of formulae (I) and (II): or a pharmaceutically acceptable salt thereof, wherein: $R_1$ is a nitrogen-containing 5 to 7-membered heteroaryl or heterocycle; $R_2$ and $R_3$ are each independently $(LQ)_m Y$, are described. The compounds are PI3K inhibitors and are useful for the treatment of cancer and immune-inflammatory diseases.

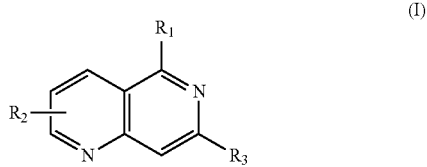

(I)

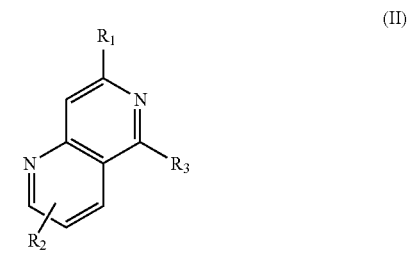

(II)

13 Claims, No Drawings

NAPHTHRIDINE DERIVATIVES AS PI3K INHIBITORS FOR THE TREATMENT OF CANCER AND IMMUNE-INFLAMMATORY DISEASE

CROSS REFERENCE TO A RELATED APPLICATION

This application is a National Stage Application of International Application Number PCT/GB2011/050824, filed Apr. 26, 2011; which claims priority to Great Britain Application No. 1007347.6, filed Apr. 30, 2010; both of which are incorporated herein by reference in their entirety.

FIELD OF THE INVENTION

The present invention relates to 1,6-naphthyridines which act as inhibitors of PI3K, for the treatment of cancer, and immune-inflammatory diseases.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation.

Compounds which are able to modulate PI3K activity have important therapeutic potential in cancer and immune and inflammatory disorders, notably organ transplant rejection.

SUMMARY OF THE INVENTION

The present invention is a compound of formula I or II

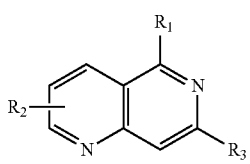

(I)

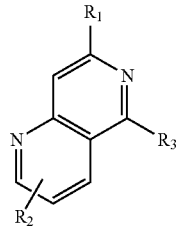

(II)

or a pharmaceutically acceptable salt thereof, wherein:
$R_1$ is a nitrogen-containing 5 to 7-membered heteroaryl or heterocycle;
$R_2$ and $R_3$ are each independently $(LQ)_m Y$;
each L is independently a direct bond, $C_1$-$C_{10}$ alkylene, $C_2$-$C_{10}$ alkenylene, $C_2$-$C_{10}$ alkynylene, arylene or $C_3$-$C_{10}$ cycloalkylene;
each Q is independently a direct bond, heteroarylene, —O—, —NR$^6$—, —C(O)—, —C(O)NR$^6$—, —SO$_2$—, —SO$_2$—NR$^6$—, —N—C(O)—NR$^6$—, —N—SO$_2$—NR$^6$, halogen, —C(halogen)$_a$(R$^6_{(2-a)}$)—, —NR$^4$R$^5$—, —C(O)NR$^4$R$^5$, where $R^4$ and $R^5$ together with the nitrogen to which they are attached form a 5 to 7-membered heterocycle linker;
m is from 0 to 5;
Y is H, $C_1$-$C_{10}$ alkyl, $C_2$-$C_{10}$ alkenyl, $C_2$-$C_{10}$ alkenyl, $C_2$-$C_{10}$ alkynyl, aryl, $C_3$-$C_{10}$ cycloalkyl, heteroaryl, —OR$^6$, —N(R$^6$)$_2$, —C(O)R$^6$, —C(O)OR$^6$, —C(O)N(R$^6$)$_2$, —N(R$^6$)$_2$, —SO$_2$—R$^6$, —SO$_2$—N(R$^6$)$_2$, —N—C(O)—N(R$^6$)$_2$, —N—SO$_2$—N(R$^6$)$_2$, halogen, —C(halogen)$_b$R$^6_{(3-b)}$, —NR$^4$R$^5$—C(O)NR$^4$R$^5$, where $R^4$ and $R^5$ together with the nitrogen to which they are attached form a 5- to 7-membered heterocycle;
b is from 1 to 3;
a is 1 or 2; and
each $R^6$ is independently H, $C_1$-$C_{10}$ alkyl, aryl or heteroaryl.

DESCRIPTION OF THE PREFERRED EMBODIMENTS

As used herein, alkyl means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, cycloalkyl contains from 3 to 10 carbon atoms. It may be monovalent or divalent. The cycloalkyl may be mono- or di-saturated. The cycloalkyl may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl)amino $C_1$-$C_3$ alkyl, bis ($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —SO$_3$H, $C_1$-$C_3$ alkylsulphonyl, aminosulfonyl, mono $C_1$-$C_3$ alkyl aminosulfonyl and bis $C_1$-$C_3$-alkyl aminosulfonyl. The cycloalkyl may contain up to 3 double bonds.

As used herein, alkenyl means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene As used herein, alkynyl is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, cycloalkyl $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl.

As used herein, aryl means a monocyclic, bicyclic, or tricyclic monovalent or divalent aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, heteroaryl means a monocyclic, bicyclic or tricyclic monovalent aromatic radical containing up to four heteroatoms selected from oxygen, nitrogen and sulfur, such as thiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulphonyl, aminosulfonyl, mono $C_1$-$C_3$ alkyl aminosulfonyl and bis $C_1$-$C_3$-alkyl aminosulfonyl.

As used herein, heterocycle is a mono- or di-valent carbocyclic radical containing up to 4 heteroatoms selected from oxygen, nitrogen and sulphur. The heterocyclic ring may be mono- or di-saturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl)amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulphonyl, aminosulfonyl, mono $C_1$-$C_3$ alkyl aminosulfonyl and bis $C_1$-$C_3$-alkyl aminosulfonyl.

As used herein, the above groups can be followed by the suffix -ene. This means that the group is divalent, i.e. a linker group.

Preferably, $R_1$ is

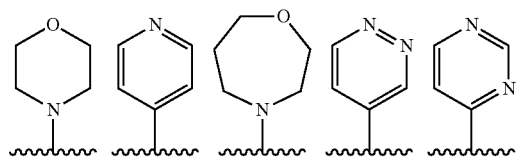

More preferably, $R_1$ is

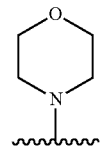 [SMILES: *N1CCOCC1]

Preferably, $R_2$ is H.

Preferably, $R_3$ is substituted aryl.

Preferably, $R_3$ is aryl substituted with at least one $C_1$-$C_3$ hydroxyalkyl.

Preferably, $R_3$ is aryl substituted with at least one $(NR^6)_2$ group.

Preferably, $R_3$ is ($C_1$-$C_{10}$ alkylene)-$NR^6$-aryl.

Preferably, $R_3$ is a bicyclic heteroaryl containing at least one nitrogen atom.

Preferably m is 0, 1 or 2.

Preferably, a compound of the invention is of any of the structures below:

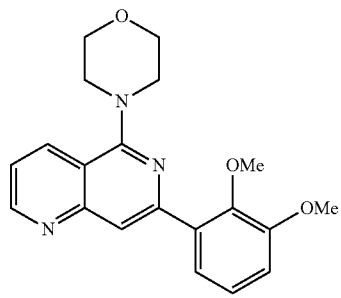

A

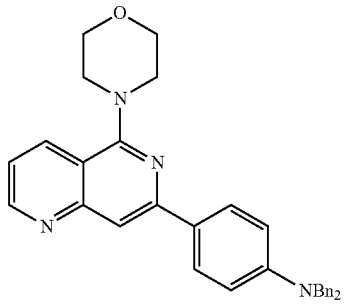

B

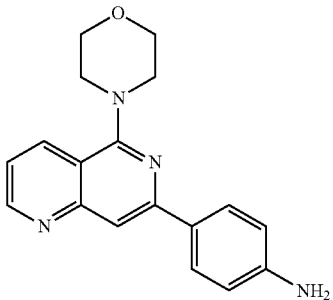

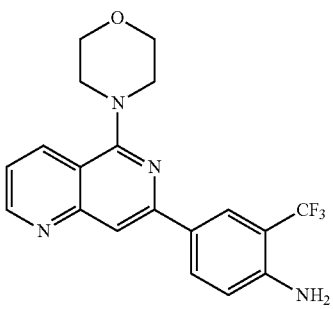

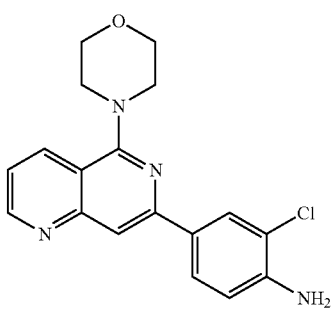

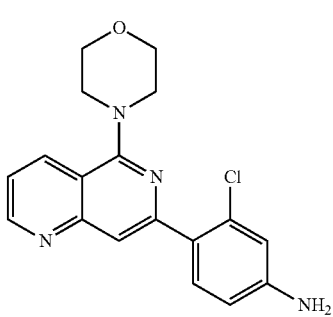

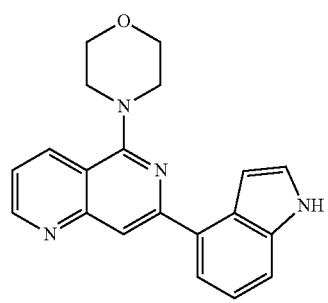

C

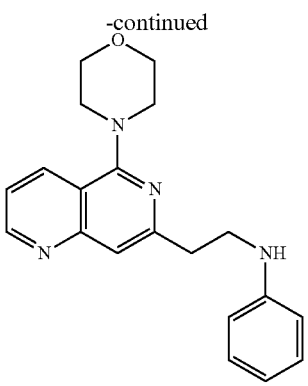

D

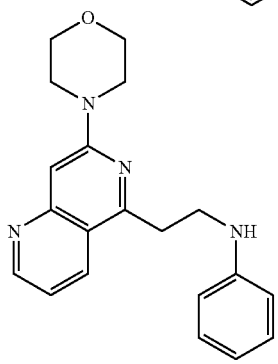

E

F

G

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, salicylic, stearic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition to be treated by a compound of the invention is rheumatoid arthritis, asthma, multiple sclerosis, psoriasis or other inflammatory skin disorders, systemic lupus, erythematosus, and organ transplant rejection. More preferably, the condition is cancer, notably leukemias including chronic myelogenous leukaemia and acute myeloid leukaemia and PTEN-negative tumours including breast, lung, brain and prostrate cancers (where PTEN refers to "phosphatise and tensin homolog deleted on chromosome 10").

The invention will now be illustrated by the following Examples.

EXAMPLES

Example A 7-(2,3-Dimethoxy-phenyl)-5-morpholin-4-yl-[1,6] naphthyridine

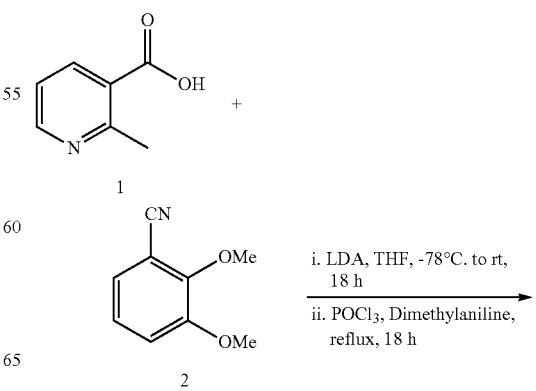

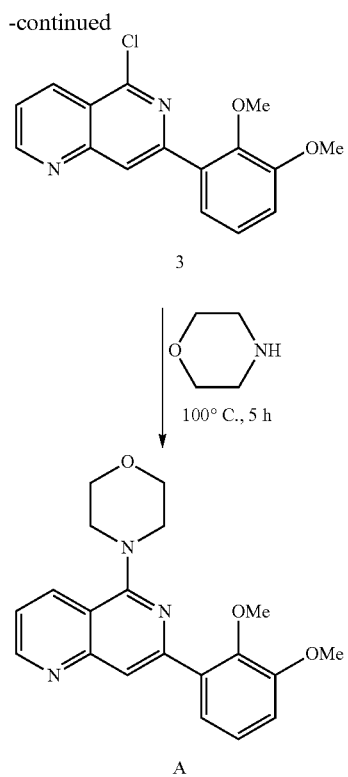

i. 5-Chloro-7-(2,3-dimethoxy-phenyl)-[1,6]naphthyridine, 3

To a suspension of 2-methylnicotinic acid, 1 (100 mg, 0.73 mmol, 1 eq) in freshly distilled THF (2 mL) was added at −78° C. a solution of LDA (910 µL, 1.83 mmol, 2.5 eq) under Ar(g). The resulting purple solution was stirred at −78° C. for 30 min, then warmed up to 0° C. for 1.5 h. It was then cooled down to −78° C. before a solution of 2,3-dimethoxy-benzonitrile, 2, (179 mg, 1.09 mmol, 1.5 eq) was added in THF (3 mL). The reaction mixture was left to warm to rt overnight, and was then quenched at 0° C. with $H_2O$ (5 mL). THF was removed in vacuo and $Et_2O$ (2 mL) was added. The solution was left to sit for 2 h until crystallization occurred. The solution was then filtered off, the filtrate was washed with $H_2O$ (3×3 mL), and then dried under high-vacuum for 5 h to give a white solid (65 mg). To a solution of this crude solid in $POCl_3$ (1.3 mL, 14.2 mmol, 20 eq) was added dimethylaniline (18 µL, 0.146 mmol, 0.20 eq). The mixture was refluxed at 110° C. under Ar(g) overnight. Once cooled down, the solution was poured very slowly into a saturated $Na_2CO_3$ solution (20 mL) at 0° C. It was then partitioned and extracted with $CH_2Cl_2$ (3×10 mL). The combined organic extracts were dried over $MgSO_4$ and the solvent was removed in vacuo. The residue was further purified by silica gel column chromatography with hexane/EtOAc (4:1) to yield the product, 3, as a pale yellow solid (56 mg, 26% over 2 steps).

$^1$H NMR (400 MHz, $CDCl_3$) $\delta_H$: 9.15 (dd, J=4.0, 2.0 Hz, 1H), 8.66 (d, J=8.0 Hz, 1H), 8.53-8.57 (m, 1H), 7.57-7.64 (m, 2H), 7.17-7.26 (m, 1H), 7.05 (dd, J=8.0, 1.5 Hz, 1H), 3.94-3.98 (m, 3H), 3.83-3.87 (m, 3H).

MS (ES$^+$) 301.1 (100%, [M+H]$^+$).

ii. 7-(2,3-Dimethoxy-phenyl)-5-morpholin-4-yl-[1,6]naphthyridine, A

A solution of 5-chloro-7-(2,3-dimethoxy-phenyl)-[1,6]naphthyridine 3 (50 mg, 0.17 mmol, 1 eq) in morpholine (1.02 mL, 11.7 mmol, 68 eq) was heated up at 100° C. for 5 h under Ar(g). Once cooled down, the solution was subsequently partitioned and extracted with $CH_2Cl_2$ (3×5 mL). The combined organic extracts were dried over $MgSO_4$ and the solvent was removed in vacuo. The residue was further purified by silica gel column chromatography with hexane/EtOAc (1:2) to furnish the product, A, as a pale yellow solid (48 mg, 81%).

$^1$H NMR (400 MHz, $CDCl_3$) $\delta_H$: 9.01 (dd, J=4.3, 1.8 Hz, 1H), 8.42 (d, J=8.5 Hz, 1H), 8.25 (s, 1H), 7.63 (dd, J=8.0, 1.5 Hz, 1H), 7.43 (dd, J=8.3, 4.3 Hz, 1H), 7.19 (t, J=8.0 Hz, 1H), 7.01 (dd, J=8.5, 1.5 Hz, 1H), 3.97-4.02 (m, 4H), 3.94 (s, 3H), 3.87 (s, 3H), 3.49-3.55 (m, 4H).

MS (ES$^+$) 352.1 (100%, [M+H]$^+$).

Example B

Dibenzyl-[4-(5-morpholin-4-yl-[1,6]naphthyridin-7-yl)-phenyl]-amine

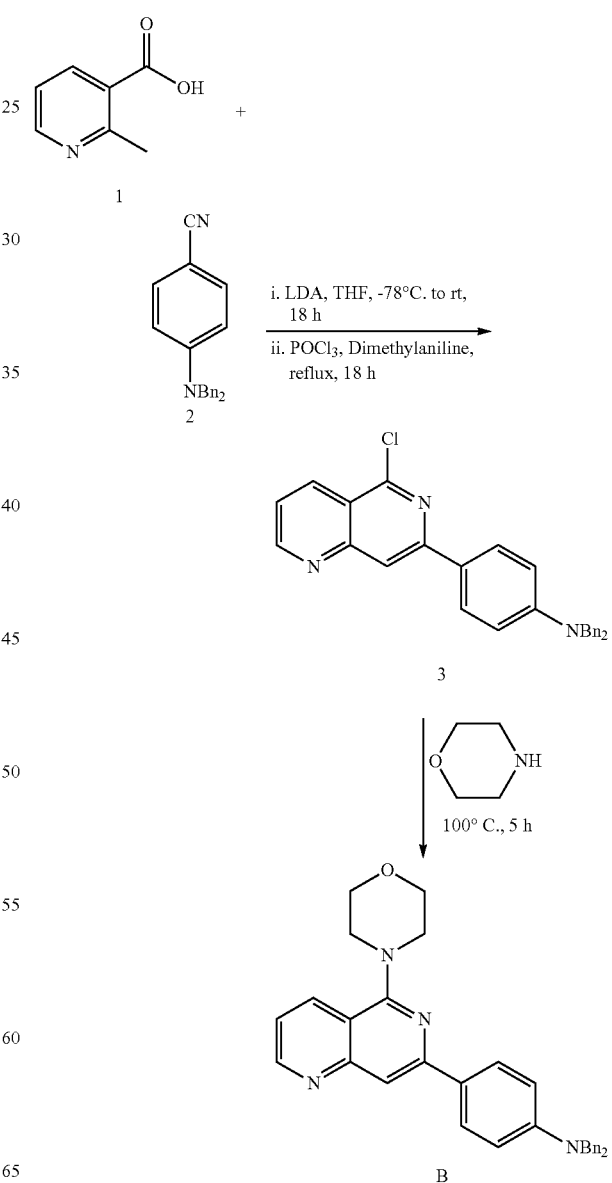

i. 4-Dibenzylamino-benzonitrile, 2

To a suspension of 4-aminobenzonitrile (1.0 g, 8.47 mmol, 1 eq), $K_2CO_3$ (5.85 g, 42.4 mmol, 5.0 eq) and KI (422 mg, 2.54 mmol, 0.3 eq) in dry DMF (10 mL) was added dropwise BnBr (4.0 mL, 33.9 mmol, 4.0 eq) under Ar(g). The reaction mixture was stirred at rt overnight, and was then partitioned with $H_2O$ (30 mL), and subsequently extracted with EtOAc (5×20 mL) and $CH_2Cl_2$ (20 mL). The combined organic extracts were dried over $MgSO_4$ and the solvent was removed in vacuo. The residue was further purified by silica gel column chromatography with hexane/EtOAc (9:1-4:1) to furnish the product, 2, as a pale yellow solid (970 mg, 38%).

$^1$H NMR (400 MHz, $CDCl_3$) $\delta_H$: 7.40-7.45 (m, 2H), 7.33-7.39 (m, 4H), 7.28-7.33 (m, 2H), 7.20 (d, J=7.0 Hz, 4H), 6.72 (d, J=9.0 Hz, 2H), 4.72 (s, 4H).

MS (ES$^+$) 321.1 (100%, [M+Na]$^+$).

ii. Dibenzyl-[4-(5-chloro-[1,6]naphthyridin-7-yl)-phenyl]-amine, 3

To a suspension of 2-methylnicotinic acid, 1 (372 mg, 2.71 mmol, 1 eq) in freshly distilled THF (8 mL) was added at −78° C. a solution of LDA (4.1 mL, 8.13 mmol, 3.0 eq) under Ar(g). The resulting purple solution was stirred at −78° C. for 30 min, and was then warmed up to 0° C. for 1.5 h. The mixture was cooled down to −78° C., and a solution of 4-dibenzylamino-benzonitrile, 2 (970 mg, 3.26 mmol, 1.2 eq) in THF (7 mL) was added. The resulting reaction mixture was left to warm up to rt overnight, and was then quenched at 0° C. with $H_2O$ (10 mL). THF was removed in vacuo and $Et_2O$ (2 mL) was added. The solution was left to sit for 2 h until crystallization occurred. The solution was filtered, the filtrate was washed with $H_2O$ (3×3 mL) then dried under high-vacuum for 5 h to furnish a yellow solid (720 mg). To a solution of this crude solid in $POCl_3$ (3.5 mL, 38.1 mmol, 22 eq) was added dimethylaniline (45 µL, 0.35 mmol, 0.20 eq), and the resulting mixture was refluxed at 110° C. under Ar(g) overnight. Once cooled down, the solution was poured very slowly into a saturated $Na_2CO_3$ solution (20 mL) at 0° C. It was then partitioned and extracted with $CH_2Cl_2$ (3×10 mL). The combined organic extracts were subsequently dried over $MgSO_4$ and the solvent was removed in vacuo. The residue was further purified by silica gel column chromatography with hexane/EtOAc (4:1-3:2) to furnish 3, as a pale yellow solid (350 mg, 30% over 2 steps).

$^1$H NMR (400 MHz, $CDCl_3$) $\delta_H$: 9.03 (dd, J=4.3, 1.8 Hz, 1H), 8.56 (d, J=8.5 Hz, 1H), 8.11 (s, 1H), 8.02 (d, J=8.5 Hz, 2H), 7.48 (dd, J=8.3, 4.3 Hz, 1H), 7.33-7.38 (m, 4H), 7.27-7.31 (m, 6H), 6.87 (d, J=9.0 Hz, 2H), 4.75 (s, 4H).

MS (ES$^+$) 436.1 (100%, [M+H]$^+$).

iii. Dibenzyl-[4-(5-morpholin-4-yl-[1,6]naphthyridin-7-yl)-phenyl]-amine, B

A solution of dibenzyl-[4-(5-chloro-[1,6]naphthyridin-7-yl)-phenyl]amine 3 (350 mg, 0.81 mmol, 1 eq) in morpholine (5.0 mL, 56 mmol, 70 eq) was heated up at 100° C. overnight under Ar(g). Once cooled down, the solution was partitioned and extracted with $CH_2Cl_2$ (3×10 mL). The combined organic extracts were dried over $MgSO_4$ and the solvent was removed in vacuo. The residue was further purified by silica gel column chromatography with hexane/EtOAc (1:1-1:3) to yield the product, B, as a pale yellow solid (242 mg, 62%).

$^1$H NMR (400 MHz, $CDCl_3$) $\delta_H$: 8.91 (dd, J=4.3, 1.8 Hz, 1H), 8.34 (d, J=8.0 Hz, 1H), 8.06 (d, J=9.0 Hz, 2H), 7.85 (s, 1H), 7.31-7.39 (m, 8H), 7.28-7.31 (m, 9H), 6.86 (d, J=9.0 Hz, 2H), 4.75 (s, 4H), 3.93-4.01 (m, 4H), 3.49-3.55 (m, 4H).

MS (ES$^+$) 487.2 (100%, [M+H]$^+$).

Example C

4-(5-Morpholin-4-yl-[1,6]naphthyridin-7-yl)phenylamine

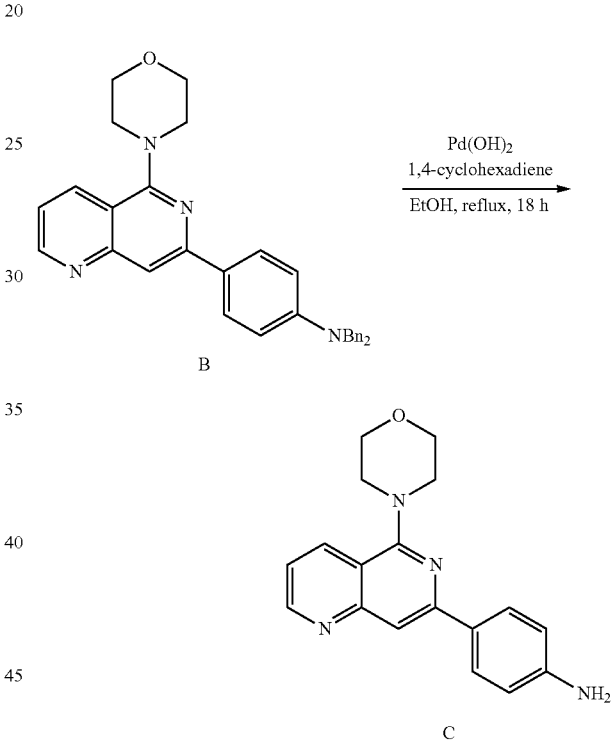

To a solution of dibenzyl-[4-(5-morpholin-4-yl-[1,6]naphthyridin-7-yl)-phenyl]-amine B (30 mg, 0.06 mmol, leg) in dry EtOH (3 mL) was added Pd(OH)$_2$ (16 mg, 50% w/w) and 1,4-cyclohexanediene (120 µL, 1.24 mmol, 20 eq) under Ar(g). The mixture was heated at 80° C. overnight; once cooled down, the reaction mixture was then filtered through a short celite pad, eluting with MeOH (10 mL). The solvent was subsequently removed in vacuo and the residue was further purified by silica gel column chromatography with hexane/EtOAc (1:4-0:1) to yield the product, C, as a pale yellow solid (9.6 mg, 51%).

$^1$H NMR (400 MHz, $CDCl_3$) $\delta_H$: 8.93 (dd, J=4.3, 1.8 Hz, 1H), 8.36 (d, J=8.0 Hz, 1H), 8.05 (d, J=8.5 Hz, 2H), 7.88 (s, 1H), 7.34 (dd, J=8.3, 4.3 Hz, 1H), 6.78 (d, J=8.5 Hz, 1H), 3.96-4.03 (m, 4H), 3.52-3.58 (m, 4H).

MS (ES$^+$) 307.1 (100%, [M+H]$^+$).

Example D

4-(5-Morpholin-4-yl-[1,6]naphthyridin-7-yl)-2-trifluoromethyl-phenylamine

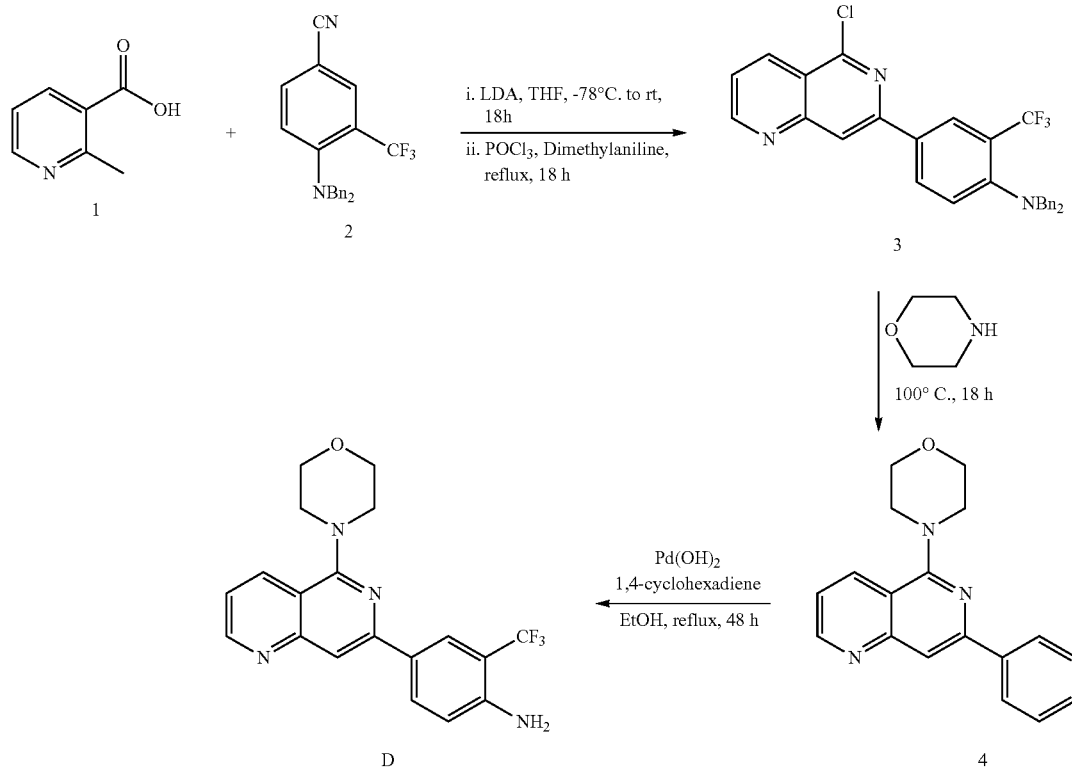

i. 4-Dibenzylamino-3-trifluoromethyl-benzonitrile, 2

To a solution of 2-amino-5-cyanobenzotrifluoride (1.0 g, 5.37 mmol, 1 eq) and benzyl bromide (2.55 mL, 21.5 mmol, 4.0 eq) in dry DMF (10 mL) was added at rt NaH (970 mg, 21.5 mmol, 4 eq) portion-wise under Ar(g). The reaction mixture was stirred at rt overnight, and was then partitioned with $H_2O$ (30 mL) and extracted with EtOAc (5×20 mL) and $CH_2Cl_2$ (20 mL). The combined organic extracts were dried over $MgSO_4$ and the solvent was removed in vacuo. The residue was further purified by silica gel column chromatography with hexane/EtOAc (1:0-9:1) to yield the product, 2, as a pale yellow solid (1.66 g, 85%).

$^1$H NMR (400 MHz, $CDCl_3$) $\delta_H$: 7.95 (d, J=2.0 Hz, 1H), 7.63 (dd, J=8.5, 1.5 Hz, 2H), 7.28-7.34 (m, 6H), 7.20 (d, J=6.5 Hz, 4H), 7.12 (d, J=8.5 Hz, 1H), 4.23 (s, 4H).

MS (ES$^+$) 389.1 (100%, [M+Na]$^+$).

ii. Dibenzyl-[4-(5-chloro-[1,6]naphthyridin-7-yl)-2-trifluoromethyl-phenyl]-amine, 3

To a suspension of 2-methylnicotinic acid, 1 (137 mg, 1.0 mmol, 1 eq) in freshly distilled THF (5 mL) was added, at −78° C., a solution of LDA (1.25 mL, 2.5 mmol, 2.5 eq) under Ar(g). The resulting purple solution was stirred at −78° C. for 30 min, and was then warmed up to 0° C. for 1.5 h. The mixture was then cooled down to −78° C. before a solution of 4-dibenzylamino-3-trifluoromethyl-benzonitrile, 2 (439 mg, 1.2 mmol, 1.2 eq) in THF (5 mL) was added. The resulting mixture was left to warm to rt overnight, was quenched at 0° C. with $H_2O$ (10 mL), then extracted with $CHCl_3$ (3×10 mL) and EtOAc (2×10 mL). The combined organic extracts were dried over $MgSO_4$ and the solvent was removed in vacuo to give a crude pale red oil (547 mg). To a solution of this residue in $POCl_3$ (2.3 mL, 24.8 mmol, 22 eq) was added dimethylaniline (30 µL, 0.35 mmol, 0.20 eq). The mixture was refluxed at 110° C. under Ar(g) overnight. Once cooled down, the solution was poured very slowly into a saturated $Na_2CO_3$ solution (50 mL) at 0° C. It was then partitioned and extracted with $CH_2Cl_2$ (3×20 mL). The combined organic extracts were dried over $MgSO_4$ and the solvent was removed in vacuo. The residue was further purified by silica gel column chromatography with hexane/EtOAc (9:1-0:1) to yield the product, 3, as a pale brown oil (100 mg, 20% over 2 steps).

$^1$H NMR (400 MHz, $CDCl_3$) $\delta_H$: 9.12 (dd, J=4.3, 1.8 Hz, 1H), 8.60-8.65 (m, 1H), 8.47 (d, J=2.0 Hz, 1H), 8.26 (d, J=1.0 Hz, 1H), 8.20 (dd, J=8.5, 2.0 Hz, 1H), 7.59 (dd, J=8.5, 4.0 Hz, 1H), 7.28-7.33 (m, 10H), 7.25 (d, J=4.5 Hz, 1H), 4.21 (s, 4H).

MS (ES$^+$) 504.1 (100%, [M+H]$^+$).

iii. Dibenzyl-[4-(5-morpholin-4-yl-[1,6]naphthyridin-7-yl)-2-trifluoromethyl-phenyl]-amine, 4

A solution of dibenzyl-[4-(5-chloro-[1,6]naphthyridin-7-yl)-2-trifluoromethyl-phenyl]-amine, 3, (100 mg, 0.20 mmol, 1 eq) in morpholine (1.25 mL, 14 mmol, 70 eq) was heated up at 100° C. overnight under Ar(g). Once cooled down, the solution was partitioned and extracted with CH$_2$Cl$_2$ (3×10 mL). The combined organic extracts were dried over MgSO$_4$ and the solvent was removed in vacuo. The residue was further purified by silica gel column chromatography with hexane/EtOAc (1:3-0:1) to yield the product as a pale yellow solid (29.1 mg, 26%).

$^1$H NMR (400 MHz, CDCl$_3$) $\delta_H$: 8.99 (dd, J=4.5, 1.5 Hz, 1H), 8.54 (d, J=2.0 Hz, 1H), 8.38 (d, J=8.5 Hz, 1H), 8.21 (dd, J=8.0, 2.0 Hz, 1H), 7.96 (s, 1H), 7.40 (ddd, J=8.8, 4.8, 4.5 Hz, 1H), 7.28-7.35 (m, 9H), 7.24-7.27 (m, 2H), 4.19 (s, 4H), 3.98-4.03 (m, 4H), 3.54-3.58 (m, 4H).

MS (ES$^+$) 577.2 (100%, [M+Na]$^+$).

iv. 4-(5-Morpholin-4-yl-[1,6]naphthyridin-7-yl)-2-trifluoromethyl-phenylamine, D To a solution of dibenzyl-[4-(5-morpholin-4-yl-[1,6]naphthyridin-7-yl)-2-trifluoromethyl-phenyl]-amine, 4 (29.1 mg, 0.06 mmol, 1 eq) in dry EtOH (3 mL) was added Pd(OH)$_2$ (15 mg, 50% w/w) and 1,4-cyclohexanediene (110 μL, 1.15 mmol, 20 eq) under Ar(g). The mixture was heated at 80° C. overnight. More Pd(OH)$_2$ (15 mg, 50% w/w) and 1,4-cyclohexanediene (110 mL, 1.15 mmol, 20 eq) were added and the mixture was again heated at 80° C. overnight. Once cooled down, the reaction mixture was filtered through a short celite pad, and eluted with MeOH (10 mL). The solvent was then removed in vacuo and the residue was further purified by silica gel column chromatography with hexane/EtOAc (0:1) to yield the product as a pale yellow solid (10.0 mg, 51%).

$^1$H NMR (400 MHz, CDCl$_3$) $\delta_H$: 8.97 (d, J=3.3 Hz, 1H), 8.40 (d, J=8.4 Hz, 1H), 8.36 (d, J=1.8 Hz, 1H), 8.14 (dd, J=8.4, 1.8 Hz, 1H), 7.92 (s, 1H), 7.40 (dd, J=8.4, 4.4 Hz, 1H), 6.86 (d, J=8.4 Hz, 1H), 4.39 (br. s., 2H), 3.97-4.03 (m, 4H), 3.54-3.60 (m, 4H).

MS (ES$^+$) 375.1 (100%, [M+H]$^+$).

Example E

2-Chloro-4-(5-morpholin-4-yl-[1,6]naphthyridin-7-yl)-phenylamine

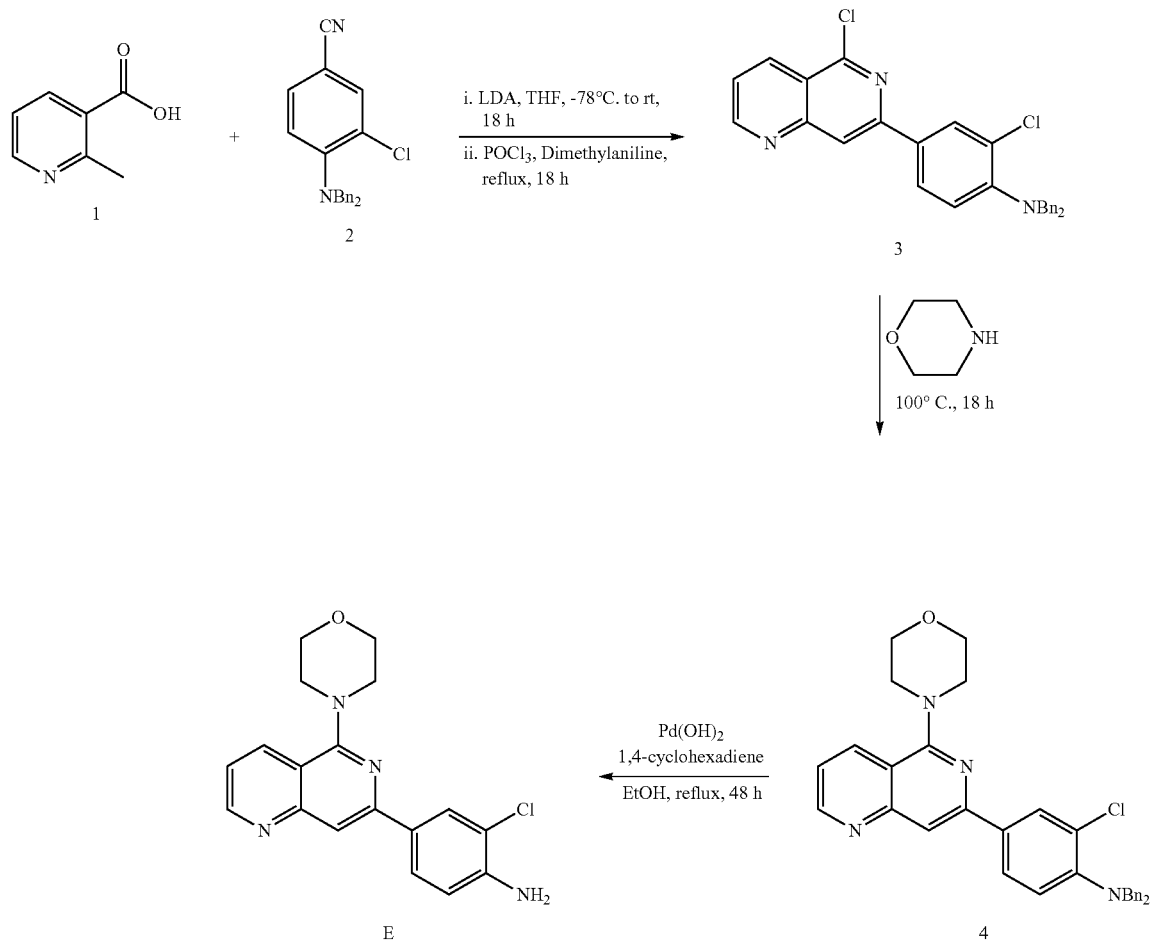

i. 3-Chloro-4-dibenzylamino-benzonitrile, 2

To a solution of 4-amino-3-chlorobenzonitrile (1.0 g, 6.56 mmol, 1 eq) and benzyl bromide (3.12 mL, 26.2 mmol, 4.0 eq) in dry DMF (10 mL) was added at rt NaH (1.31 g, 32.8 mmol, 5 eq) portionwise under Ar(g). The reaction mixture was stirred at rt overnight, and was subsequently partitioned with $H_2O$ (30 mL) and extracted with EtOAc (5×20 mL) and $CH_2Cl_2$ (20 mL). The combined organic extracts were dried over $MgSO_4$ and the solvent was removed in vacuo. The residue was further purified by silica gel column chromatography with hexane/EtOAc (1:0-9:1) to furnish 2 as a white solid (2.09 g, 96%).

$^1$H NMR (400 MHz, CDCl$_3$) $\delta_H$: 7.68 (d, J=2.0 Hz, 1H), 7.28-7.37 (m, 6H), 7.26 (d, J=2.5 Hz, 5H), 6.92 (d, J=8.5 Hz, 1H), 4.34 (s, 4H).

MS (ES$^+$) 355.1 (100%, [M+Na]$^+$).

ii. Dibenzyl-[2-chloro-4-(5-chloro-[1,6]naphthyridin-7-yl)-phenyl]-amine, 3

To a suspension of 2-methylnicotinic acid, 1 (274 mg, 2.0 mmol, 1 eq) in freshly distilled THF (5 mL) was added at −78° C. a solution of LDA (2.5 mL, 5.0 mmol, 2.5 eq) under Ar(g). The resulting purple solution was stirred at −78° C. for 30 min, then warmed up to 0° C. for 1.5 h. The solution was then cooled down to −78° C., and a solution of 3-chloro-4-dibenzylamino-benzonitrile, 2 (800 mg, 2.4 mmol, 1.2 eq) in THF (5 mL) was added. The reaction mixture was left to warm up to rt overnight, was subsequently quenched at 0° C. with $H_2O$ (20 mL), and then extracted with CHCl$_3$ (3×10 mL) and EtOAc (2×10 mL). The combined organic extracts were dried over $MgSO_4$ and the solvent was removed in vacuo to produce a crude pale red oil (1.03 g). To a solution of this residue in POCl$_3$ (4.0 mL, 44 mmol, 22 eq) was added dimethylaniline (51 μL, 0.4 mmol, 0.20 eq). The mixture was refluxed at 100° C. under Ar(g) overnight. Once cooled down, the solution was poured very slowly into a saturated Na$_2$CO$_3$ solution (50 mL) at 0° C., and was then partitioned and extracted with $CH_2Cl_2$ (3×20 mL). The combined organic extracts were dried over $MgSO_4$ and the solvent was removed in vacuo. The residue was further purified by silica gel column chromatography with hexane/EtOAc (3:1-0:1) to yield an inseparable mixture of the product, 3 and a by-product, benzyl-[2-chloro-4-(5-chloro-[1,6]naphthyridin-7-yl)-phenyl]-amine as a pale yellow oil (120 mg, 1:1.4 ratio; 3=6%, by-product=9% over 2 steps).

$^1$H NMR (400 MHz, CDCl$_3$) $\delta_H$: 3-9.10 (dd, J=4.5, 1.5 Hz, 1H), 8.58 (d, J=9.5 Hz, 1H), 8.27 (d, J=2.0 Hz, 1H), 8.18 (s, 1H), 7.85 (d, J=2.0 Hz, 1H), 7.56 (dd, J=8.5, 4.5 Hz, 1H), 7.22-7.42 (m, 10H), 7.03 (d, J=8.0 Hz, 1H), 4.33 (s, 4H).

MS (ES$^+$) 470.0 (100%, [M+H]$^+$).

$^1$H NMR (400 MHz, CDCl$_3$) $\delta_H$: benzyl-[2-chloro-4-(5-chloro-[1,6]naphthyridin-7-yl)-phenyl]-amine by-product—9.06 (dd, J=4.3, 1.8 Hz, 1H), 8.58 (d, J=9.5 Hz, 1H), 8.21 (d, J=2.0 Hz, 1H), 8.12 (s, 1H), 7.92 (dd, J=8.5, 2.0 Hz, 1H), 7.51 (dd, J=8.5, 4.0 Hz, 1H), 7.21-7.42 (m, 5H), 6.76 (d, J=8.5 Hz, 1H), 4.99-5.09 (m, 1H), 4.51 (d, J=4.5 Hz, 2H).

MS (ES$^+$) 380.0 (100%, [M+H]$^+$).

iii. Dibenzyl-[2-chloro-4-(5-morpholin-4-yl-[1,6]naphthyridin-7-yl)-phenyl]-amine, 4

A solution of the mixture of 3 and benzyl-[2-chloro-4-(5-chloro-[1,6]naphthyridin-7-yl)-phenyl]-amine (120 mg, 1:1.4, 0.26 mmol, 1 eq) in morpholine (1.6 mL, 18 mmol, 70 eq) was heated up at 100° C. overnight under Ar(g). Once cooled, the solvent was removed in vacuo and the resulting residue purified by silica gel column chromatography with hexane/EtOAc (1:3-1:4) to yield an inseparable mixture of the product 4 and a by-product, benzyl-[2-chloro-4-(5-morpholin-4-yl-[1,6]naphthyridin-7-yl)-phenyl]-amine as a pale yellow solid (107 mg, 1:1.4; 4=70%, by-product=79%).

$^1$H NMR (400 MHz, CDCl$_3$) $\delta_H$: 4-8.98 (dd, J=4.3, 1.8 Hz, 1H), 8.35 (d, J=8.5 Hz, 1H), 8.29 (d, J=2.0 Hz, 1H), 7.89 (s, 1H), 7.89 (dd, J=8.5, 2.0 Hz, 1H), 7.20-7.43 (m, 10H), 7.04 (d, J=8.0 Hz, 1H), 4.31 (s, 4H), 3.96-4.02 (m, 4H), 3.50-3.57 (m, 4H).

MS (ES$^+$) 521.3 (100%, [M+H]$^+$).

$^1$H NMR (400 MHz, CDCl$_3$) $\delta_H$: benzyl-[2-chloro-4-(5-morpholin-4-yl-[1,6]naphthyridin-7-yl)-phenyl]-amine—8.94 (dd, J=4.3, 1.8 Hz, 1H), 8.35 (d, J=8.5 Hz, 1H), 8.20 (d, J=2.0 Hz, 1H), 7.94 (dd, J=8.5, 2.0 Hz, 1H), 7.84 (s, 1H), 7.21-7.42 (m, 5H), 6.74 (d, J=8.5 Hz, 1H), 5.00 (br. s., 1H), 4.51 (d, J=5.5 Hz, 2H), 3.95-4.03 (m, 4H), 3.49-3.57 (m, 4H).

MS (ES$^+$) 431.1 (100%, [M+H]$^+$).

iv. 2-Chloro-4-(5-morpholin-4-yl-[1,6]naphthyridin-7-yl)-phenylamine, E

To the mixture of 4 and benzyl-[2-chloro-4-(5-morpholin-4-yl-[1,6]naphthyridin-7-yl)-phenyl]-amine (60 mg, 1:1.4, 0.128 mmol, 1 eq) in dry EtOH (3 mL) was added Pd(OH)$_2$ (30 mg, 50% w/w) and 1,4-cyclohexanediene (240 μL, 2.56 mmol, 20 eq) under Ar(g). The mixture was heated at 80° C. overnight. Additional quantities of Pd(OH)$_2$ (30 mg, 50% w/w) and 1,4-cyclohexanediene (240 μL, 2.56 mmol, 20 eq) were then added, and the mixture was again heated at 80° C. overnight. Once cooled down, the reaction mixture was filtered through a short celite pad, and eluted with MeOH (10 mL). The solvent was then removed in vacuo and the residue was further purified by silica gel column chromatography using hexane/EtOAc (1:9-0:1) as eluant to furnish E as a pale yellow solid (11.2 mg, 26%).

$^1$H NMR (400 MHz, CDCl$_3$) $\delta_H$: 8.95 (dd, J=4.0, 1.5 Hz, 1H), 8.35 (d, J=8.0 Hz, 1H), 8.17 (d, J=2.0 Hz, 1H), 7.91 (dd, J=8.5, 2.0 Hz, 1H), 7.85 (s, 1H), 7.35 (dd, J=8.3, 4.3 Hz, 1H), 6.87 (d, J=8.5 Hz, 1H), 4.25 (br. s., 2H), 3.96-4.03 (m, 4H), 3.51-3.57 (m, 4H).

MS (ES$^+$) 341.1 (100%, [M+H]$^+$).

Example F

3-Chloro-4-(5-morpholin-4-yl-[1,6]naphthyridin-7-yl)-phenylamine

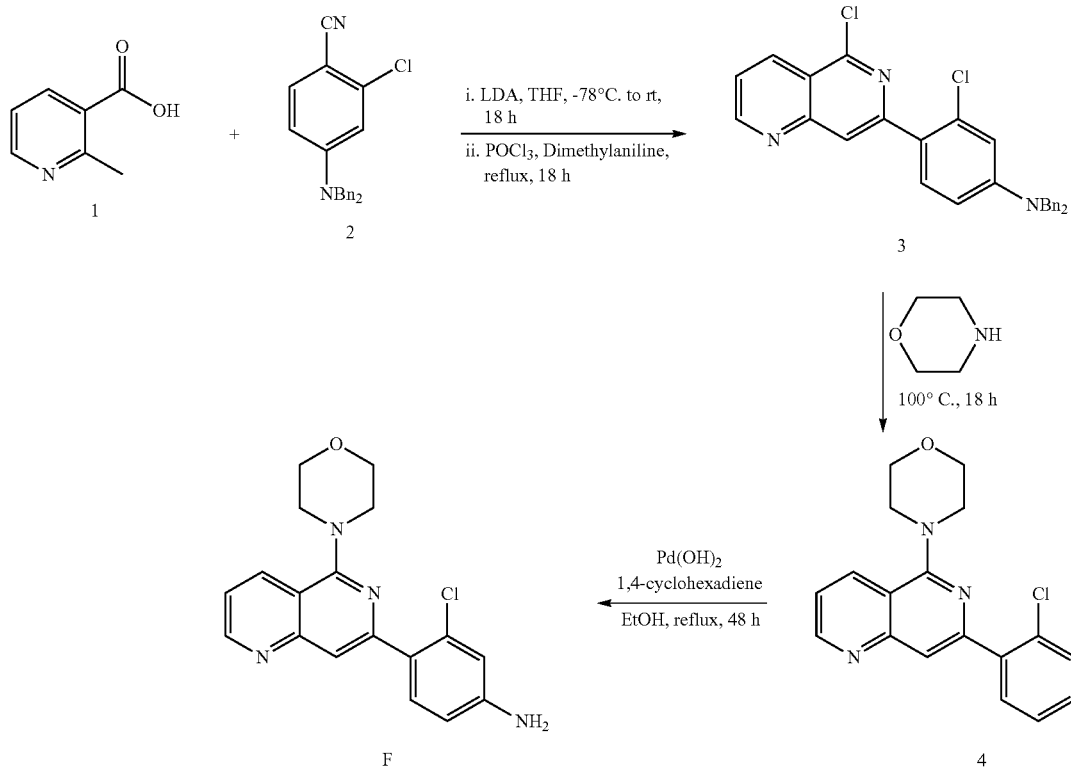

3-Chloro-4-(5-morpholin-4-yl-[1,6]naphthyridin-7-yl)-phenylamine, F i. 2-Chloro-4-dibenzylamino-benzonitrile, 2

To a solution of 4-amino-2-chlorobenzonitrile (1.0 g, 6.56 mmol, 1 eq) and benzyl bromide (3.12 mL, 26.2 mmol, 4.0 eq) in dry DMF (10 mL) was added at rt NaH (1.31 g, 32.8 mmol, 5 eq) portionwise under Ar(g). The reaction mixture was stirred at rt overnight, and was subsequently partitioned with H$_2$O (30 mL) and extracted with EtOAc (5×20 mL) and CH$_2$Cl$_2$ (20 mL). The combined organic extracts were dried over MgSO$_4$ and the solvent was removed in vacuo. The residue was further purified by silica gel column chromatography with hexane/EtOAc (1:0-9:1) to yield the product, 2, as a white solid (1.72 g, 79%);

$^1$H NMR (400 MHz, CDCl$_3$) $\delta_H$: 7.31-7.41 (m, 7H), 7.19 (d, J=7.0 Hz, 4H), 6.78 (d, J=2.5 Hz, 1H), 6.61 (dd, J=9.0, 2.5 Hz, 1H), 4.70 (s, 4H).

MS (ES$^+$) 355.0 (100%, [M+Na]$^+$).

ii. Dibenzyl-[3-chloro-4-(5-chloro-[1,6]naphthyridin-7-yl)-phenyl]-amine, 3

To a suspension of 2-methylnicotinic acid, 1 (274 mg, 2.0 mmol, 1 eq) in freshly distilled THF (5 mL) was added at –78° C. a solution of LDA (2.5 mL, 5.0 mmol, 2.5 eq) under Ar(g). The resulting purple solution was stirred at –78° C. for 30 min, and then warmed up to 0° C. for 1.5 h. The mixture was then cooled down to –78° C., and a solution of 2-chloro-4-dibenzylamino-benzonitrile, 2 (800 mg, 2.4 mmol, 1.2 eq) in THF (5 mL) was added. The reaction mixture was left to warm up to rt overnight, and was then quenched at 0° C. with H$_2$O (20 mL), and extracted with CHCl$_3$ (3×10 mL) and EtOAc (2×10 mL). The combined organic extracts were dried over MgSO$_4$ and the solvent was removed in vacuo to give a crude pale red oil (1.15 g). To a solution of this residue in POCl$_3$ (4.0 mL, 44 mmol, 22 eq) was added dimethylaniline (51 µL, 0.4 mmol, 0.20 eq). The mixture was refluxed at 100° C. under Ar(g) overnight; once cooled down, the solution was poured very slowly into a saturated Na$_2$CO$_3$ solution (50 mL) at 0° C., and was then partitioned and extracted with CH$_2$Cl$_2$ (3×20 mL). The combined organic extracts were dried over MgSO$_4$ and the solvent was removed in vacuo. The residue was further purified by silica gel column chromatography with hexane/EtOAc (3:1-0:1) to yield an inseparable mixture of the product, 3, and the by-product benzyl-[3-chloro-4-(5-chloro-[1,6]naphthyridin-7-yl)-phenyl]-amine as a pale yellow oil (183 mg, 1:1 ratio; 3=10%, by-product=12% over 2 steps)

$^1$H NMR (400 MHz, CDCl$_3$) $\delta_H$: 3-9.11 (dd, J=4.2, 1.6 Hz, 1H), 8.58-8.63 (m, 1H), 8.27 (s, 1H), 7.71 (d, J=7.7 Hz, 1H), 7.56 (dd, J=8.4, 4.4 Hz, 1H), 7.23-7.47 (m, 10H), 6.77 (dd, J=8.8, 2.6 Hz, 1H), 4.71 (s, 4H).

MS (ES$^+$) 470.1 (100%, [M+H]$^+$).

$^1$H NMR (400 MHz, CDCl$_3$) $\delta_H$: benzyl-[3-chloro-4-(5-chloro-[1,6]naphthyridin-7-yl)-phenyl]-amine—9.15 (dd, J=4.2, 1.6 Hz, 1H), 8.66 (dd, J=8.4, 0.7 Hz, 1H), 8.25 (s, 1H), 7.60-7.68 (m, 2H), 7.22-7.54 (m, 5H), 6.88 (d, J=2.6 Hz, 1H), 4.91 (s, 1H), 3.81 (d, J=3.3 Hz, 2H).

MS (ES$^+$) 380.0 (100%, [M+H]$^+$).

iii. Dibenzyl-[3-chloro-4-(5-morpholin-4-yl-[1,6] naphthyridin-7-yl)-phenyl]-amine, 4

A mixture of 3 and benzyl-[3-chloro-4-(5-chloro-[1,6] naphthyridin-7-yl)-phenyl]-amine (180 mg, 1:1, 0.38 mmol, 1 eq) in morpholine (2.4 mL, 27 mmol, 70 eq) was heated up at 100° C. overnight under Ar(g). Once cooled down, the solvent was removed in vacuo, and the resulting residue was purified by silica gel column chromatography, eluting with hexane/EtOAc (1:2-0:1) to yield an inseparable mixture of the product 4 and the by-product benzyl-[3-chloro-4-(5-morpholin-4-yl-[1,6]naphthyridin-7-yl)-phenyl]-amine as a pale yellow solid (167 mg, 1:1; 4=84%, by-product=99%).

$^1$H NMR (400 MHz, CDCl$_3$) $\delta_H$: 4-8.98 (dd, J=4.3, 1.8 Hz, 1H), 8.34-8.41 (m, 1H), 7.92 (s, 1H), 7.70 (s, 1H), 7.43 (dd, J=8.3, 4.3 Hz, 1H), 7.22-7.40 (m, 11H), 6.76 (dd, J=8.5, 2.5 Hz, 1H), 4.71 (s, 4H), 3.93-3.99 (m, 4H), 3.49 (m, 4H).

MS (ES$^+$) 521.2 (100%, [M+H]$^+$).

$^1$H NMR (400 MHz, CDCl$_3$) $\delta_H$: benzyl-[3-chloro-4-(5-morpholin-4-yl-[1,6]naphthyridin-7-yl)-phenyl]-amine— eq) under Ar(g). The mixture was heated at 80° C. overnight. Additional quantities of Pd(OH)$_2$ (60 mg, 40% w/w) and 1,4-cyclohexanediene (400 μL, 4.10 mmol, 15 eq) were added, and the mixture was again heated at 80° C. overnight. Once cooled down, the reaction mixture was filtered through a short celite pad, eluted with MeOH (10 mL). The solvent was removed in vacuo and the residue was further purified by silica gel column chromatography, eluting with CH$_2$Cl$_2$/MeOH (1:0-49:1), to furnish the product, F, as a pale yellow solid (8.1 mg, 8%).

$^1$H NMR (400 MHz, CDCl$_3$) $\delta_H$: 8.99 (dd, J=4.5, 1.5 Hz, 1H), 8.41 (d, J=8.5 Hz, 1H), 7.94 (s, 1H), 7.63 (d, J=8.0 Hz, 1H) 7.42 (dd, J=8.3, 4.3 Hz, 1H), 6.83 (d, J=2.5 Hz, 1H), 6.70 (dd, J=8.5, 2.5 Hz, 1H), 3.93-4.01 (m, 4H), 3.47-3.55 (m, 4H).

MS (ES$^+$) 341.1 (100%, [M+H]$^+$).

Example G 7-(1H-Indol-4-yl)-5-morpholin-4-yl-1,6-naphthyridine

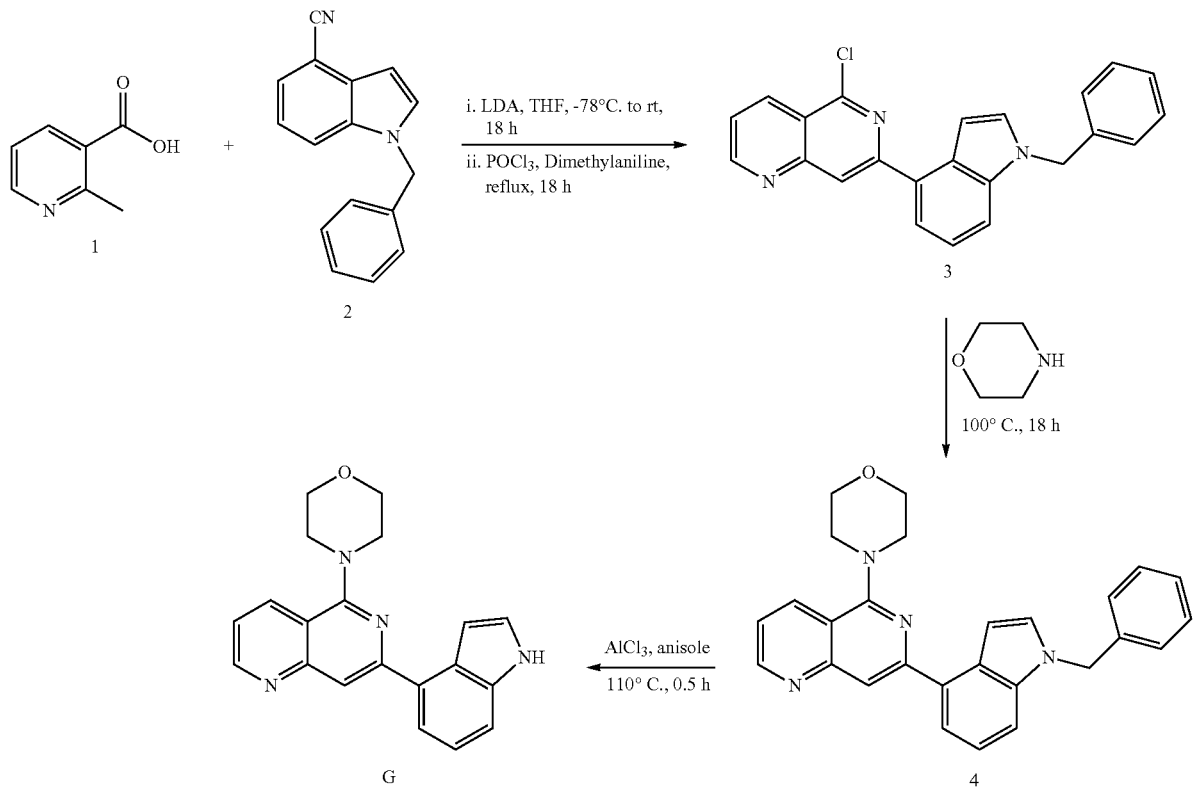

i. 1-Benzyl-1H-indole-4-carbonitrile, 2

To a solution of indole-4-carbonitrile (2.0 g, 14.1 mmol, 1 eq) and benzyl bromide (2.17 mL, 18.3 mmol, 1.3 eq) in dry DMF (20 mL) was added, at rt, NaH (733 mg, 18.3 mmol, 1.3 eq) portionwise under Ar(g). The resulting reaction mixture was stirred at rt overnight, and was subsequently partitioned with H$_2$O (30 mL), and then extracted with EtOAc (3×20 mL) and CH$_2$Cl$_2$ (20 mL). The combined organic extracts were dried over MgSO$_4$ and the solvent was removed in vacuo. The residue was further purified by silica gel column chromatography with hexane/EtOAc (9:1-1:3) to furnish the product, 2, as a white solid (3.30 g, 99%).

9.01 (dd, J=4.3, 1.8 Hz, 1H), 8.39 (d, J=9.0 Hz, 1H), 7.88 (s, 1H), 7.66 (d, J=8.5 Hz, 1H), 7.64 (d, J=1.5 Hz, 1H), 7.23-7.40 (m, 6H), 6.88 (d, J=3.0 Hz, 1H), 4.91 (s, 1H), 3.92-3.99 (m, 4H), 3.83 (m, 2H), 3.49 (d, J=3.4 Hz, 4H).

MS (ES$^+$) 431.1 (100%, [M+H]$^+$).

iv. 3-Chloro-4-(5-morpholin-4-yl-[1,6]naphthyridin-7-yl)-phenylamine, F

To a mixture of 4 and benzyl-[3-chloro-4-(5-morpholin-4-yl-[1,6]naphthyridin-7-yl)-phenyl]-amine (164 mg, 0.32 mmol, 1 eq) in dry EtOH (3 mL) was added Pd(OH)$_2$ (60 mg, 40% w/w) and 1,4-cyclohexanediene (600 μL, 6.30 mmol, 20

¹H NMR (400 MHz, CDCl₃) δ_H: 7.49 (t, J=8.6 Hz, 2H), 7.29-7.36 (m, 4H), 7.18-7.23 (m, 1H), 7.07-7.13 (m, 2H), 6.75-6.80 (m, 1H), 5.38 (s, 2H).

MS (ES⁺) 255.2 (100%, [M+Na]⁺).

ii. 7-(1-Benzyl-1H-indol-4-yl)-5-chloro-1,6-naphthyridine, 3

To a suspension of 2-methylnicotinic acid, 1 (274 mg, 2.0 mmol, 1 eq) in freshly distilled THF (5 mL) was added, at −78° C., a solution of LDA (2.5 mL, 5.0 mmol, 2.5 eq) under Ar(g). The resulting purple solution was stirred at −78° C. for 30 mins, and was then warmed up to 0° C. for 1.5 h. The solution was then cooled to −78° C., and a solution of 1-benzyl-1H-indole-4-carbonitrile (558 mg, 2.4 mmol, 1.2 eq) in THF (5 mL) was added. The resulting reaction mixture was left to warm to rt overnight, and was then quenched at 0° C. with H₂O (20 mL), and extracted with CHCl₃ (3×10 mL) and EtOAc (2×10 mL). The combined organic extracts were dried over MgSO₄ and the solvent was removed in vacuo to give a crude oil (800 mg). To a solution of this residue in POCl₃ (4.6 mL, 50 mmol, 22 eq) was added dimethylaniline (60 mL, 0.45 mmol, 0.20 eq). The mixture was refluxed at 100° C. under Ar(g) overnight. Once cooled down, the solution was poured very slowly into a half saturated Na₂CO₃ solution (50 mL) at 0° C. It was then partitioned and extracted with CH₂Cl₂ (3×20 mL). The combined organic extracts were subsequently dried over MgSO₄ and the solvent was removed in vacuo. The residue was further purified by silica gel column chromatography with hexane/EtOAc (9:1-1:3) to yield the product, 3, as a pale yellow oil (104 mg, 14% over 2 steps).

¹H NMR (400 MHz, CDCl₃) δ_H: 9.13 (dd, J=4.0, 1.5 Hz, 1H), 8.66 (ddd, J=8.7, 1.3, 1.1 Hz, 1H), 8.43 (s, 1H), 7.77-7.80 (m, 1H), 7.56-7.61 (m, 1H), 7.39-7.43 (m, 1H), 7.28-7.36 (m, 5H), 7.23-7.25 (m, 1H), 7.13-7.17 (m, 2H), 5.42 (s, 2H).

MS (ES⁺) 370.0 (100%, [M+H]⁺).

iii. 7-(1-Benzyl-1H-indol-4-yl)-5-morpholin-4-yl-1,6-naphthyridine, 4

A flask charged with 7-(1-benzyl-1H-indol-4-yl)-5-chloro-1,6-naphthyridine, 3 (94 mg, 0.25 mmol, 1 eq) and morpholine (1.6 mL, 18 mmol, 70 eq) was heated at 100° C. overnight under Ar(g). Once cooled down, the solvent was removed in vacuo, and the residue was purified by silica gel column chromatography with hexane/EtOAc (3:2-0:1) to yield the product as pale yellow solid (96 mg, 91%).

¹H NMR (400 MHz, CDCl₃) δ_H: 9.01 (dd, J=4.3, 1.8 Hz, 1H), 8.42 (d, J=7.6 Hz, 1H), 8.12 (s, 1H), 7.77-7.82 (m, 1H), 7.39-7.43 (m, 1H), 7.29-7.39 (m, 5H), 7.24-7.27 (m, 2H), 7.14-7.18 (m, 2H), 5.41 (s, 2H), 4.00-4.05 (m, 5H), 3.55-3.60 (m, 5H).

MS (ES⁺) 421.1 (100%, [M+H]⁺).

iv. 7-(1H-Indol-4-yl)-5-morpholin-4-yl-1,6-naphthyridine, G

To a solution of 7-(1-benzyl-1H-indol-4-yl)-5-morpholin-4-yl-1,6-naphthyridine, 4 (64 mg, 0.13 mmol, 1 eq) in dry anisole (1.5 mL) was added a suspension of AlCl₃ in dry anisole (1.5 mL). The mixture was then heated at 110° C. for 0.5 h. Once cooled down, it was partitioned with H₂O (15 mL) and extracted with EtOAc (3×20 mL) and CH₂Cl₂ (20 mL). The combined organic extracts were then dried over MgSO₄ and the solvent was removed in vacuo. The residue was further purified by silica gel column chromatography with CH₂Cl₂/MeOH (1:0-49:1) to yield the product, G, as a pale yellow solid (7.8 mg, 15%).

¹H NMR (400 MHz, CDCl₃) δ_H: 9.01 (dd, J=4.3, 1.8 Hz, 1H), 8.42 (d, J=8.6 Hz, 1H), 8.35 (br. s., 1H), 8.12 (s, 1H), 7.77-7.84 (m, 1H), 7.49 (d, J=8.1 Hz, 1H), 7.41 (dd, J=8.6, 4.0 Hz, 1H), 7.32-7.38 (m, 2H), 7.25-7.27 (m, 1H), 4.00-4.05 (m, 4H), 3.55-3.60 (m, 4H).

MS (ES⁺) 331.0 (100%, [M+H]⁺).

In Vitro Data:

| COMPOUND | Biochemical IC₅₀, PI3K-p110β (μM) | IC₅₀, MCF7 Breast Tumour Cell Growth Inhibition (μM) |
|---|---|---|
| E | 0.69 | 6.06 |
| F | 3.7 | 10.87 |

| COMPOUND | IC₅₀ PI3K-p110α (μM) | IC₅₀ PI3K-p110β (μM) | IC₅₀ PI3K-p110δ (μM) | IC₅₀ PI3K-p110γ (μM) |
|---|---|---|---|---|
| G | >10 | 3.4 | 0.26 | >10 |

The invention claimed is:

1. A compound of formula I or II

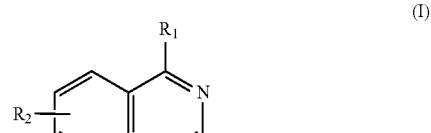

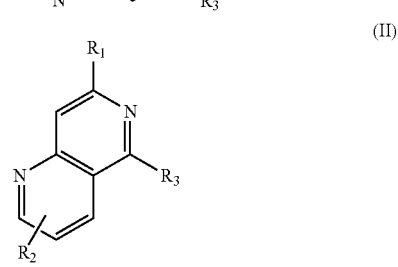

or a pharmaceutically acceptable salt thereof, wherein:
R₁ is selected from the group consisting of:

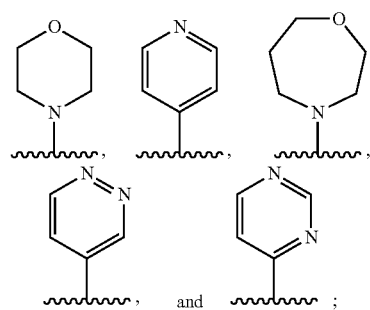

R₂ is (LQ)_mY;
each L is independently selected from the group consisting of: a direct bond, C₁-C₁₀ alkylene, C₂-C₁₀ alkenylene, C₂-C₁₀ alkynylene, arylene and C₃-C₁₀ cycloalkylene;
each Q is independently selected from the group consisting of: a direct bond, heteroarylene, —O—, —NR⁶—, —C(O)—, —C(O)NR⁶—, —SO₂—, —SO₂—NR⁶—, —NH—C(O)—NR⁶—, —NH—SO₂—NR⁶, —C(halogen)$_a$(R⁶$_{(2-a)}$)—, —NR⁴R⁵—, and —C(O)NR⁴R⁵, where R⁴ and R⁵ together with the nitrogen to which they are attached form a 5 to 7-membered heterocycle linker;

m is from 0 to 5;

Y is independently selected from the group consisting of: H, C₁-C₁₀ alkyl, C₂-C₁₀ alkenyl, C₂-C₁₀ alkynyl, aryl, C₃-C₁₀ cycloalkyl, heteroaryl, —OR⁶, —N(R⁶)₂, —C(O)R⁶, —C(O)OR⁶, —C(O)N(R⁶)₂, —SO₂—R⁶, —SO₂—N(R⁶)₂, —NH—C(O)—N(R⁶)₂, —NH—SO₂—N(R⁶)₂, halogen, —C(halogen)$_b$R⁶$_{(3-b)}$;

b is from 1 to 3;

a is 1 or 2;

R₃ is selected from the group consisting of:
(a) aryl substituted with from one to five substituents independently selected from the group of C₁-C₃ hydroxyalkyl, —N(benzyl)₂, C₂-C₁₀ alkenyl, C₂-C₁₀ alkynyl, aryl, C₃-C₁₀ cycloalkyl, heteroaryl, —OR⁶, —N(R⁶)₂, —C(O)R⁶, —C(O)OR⁶, —C(O)N(R⁶)₂, —SO₂—R⁶, —SO₂—N(R⁶)₂, —NH—C(O)—N(R⁶)₂, —NH—SO₂—N(R⁶)₂, halogen, and —C(halogen)$_b$R⁶$_{(3-b)}$;
(b) (C₁-C₁₀ alkylene)-NR⁶-aryl; and
(c) a bicyclic heteroaryl containing at least one nitrogen atom; and each R⁶ is independently selected from the group consisting of H, C₁-C₁₀ alkyl, aryl or heteroaryl.

2. The compound according to claim 1, wherein R₁ is

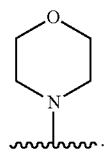

3. The compound according to claim 1, wherein R₂ is H.

4. The compound according to claim 1, wherein R₃ is aryl substituted with from one to five substituents each independently selected from the group consisting of: C₁-C₃ hydroxyalkyl, —N(benzyl)₂, C₂-C₁₀ alkenyl, C₂-C₁₀ alkynyl, aryl, C₃-C₁₀ cycloalkyl, heteroaryl, —OR⁶, —N(R⁶)₂, —C(O)R⁶, —C(O)OR⁶, —C(O)N(R⁶)₂, —SO₂—R⁶, —SO₂—N(R⁶)₂, —NH—C(O)—N(R⁶)₂, —NH—SO₂—N(R⁶)₂, halogen, and —C(halogen)$_b$R⁶$_{(3-b)}$.

5. The compound according to claim 4, wherein R₃ is aryl substituted with at least one C₁-C₃ hydroxyalkyl.

6. The compound according to claim 4, wherein R₃ is aryl substituted with at least one (NR⁶)₂ group.

7. The compound according to claim 1, wherein R₃ is (C₁-C₁₀ alkylene)-NR⁶-aryl.

8. The compound according to claim 1, which has a structure selected from:

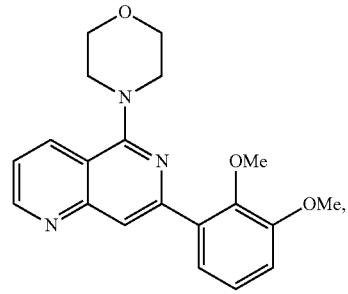

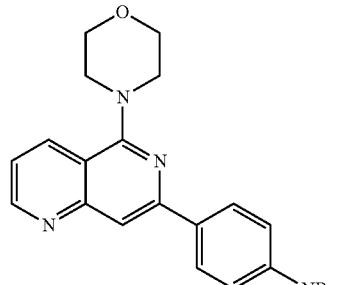

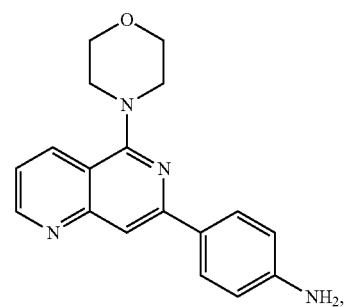

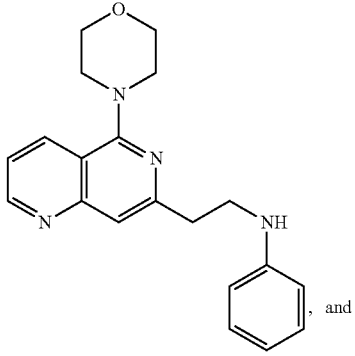

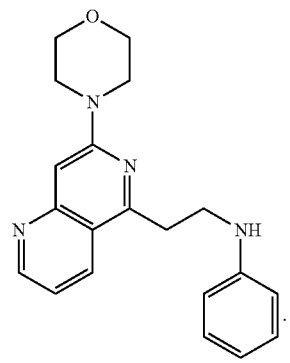

9. The compound according to claim 1, which is compound G:

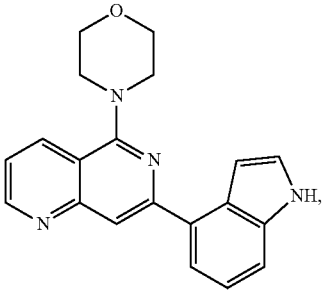 [SMILES: c1cc(-c2cc3ncccc3c(N3CCOCC3)n2)c2cc[nH]c2c1]

or a pharmaceutically acceptable salt thereof.

10. The compound according to claim 1, wherein $R_3$ is a bicyclic heteroaryl containing at least one nitrogen atom.

11. The compound according to claim 1, wherein $R_3$ is indolyl.

12. A compound of formula I or II

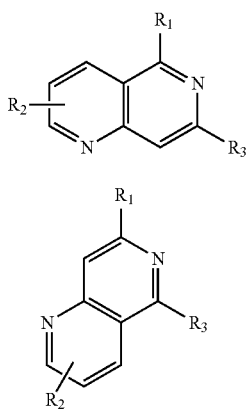

or a pharmaceutically acceptable salt thereof, wherein:

$R_1$ is

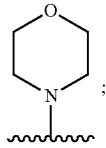 [SMILES: *N1CCOCC1]

$R_2$ is $(LQ)_m Y$;

each L is independently selected from the group consisting of: a direct bond, $C_1$-$C_{10}$ alkylene, $C_2$-$C_{10}$ alkenylene, $C_2$-$C_{10}$ alkynylene, arylene and $C_3$-$C_{10}$ cycloalkylene;

each Q is independently selected from the group consisting of: a direct bond, heteroarylene, —O—, —NR$^6$—, —C(O)—, —C(O)NR$^6$—, —SO$_2$—, —SO$_2$—NR$^6$—, —NH—C(O)—NR$^6$—, —NH—SO$_2$—NR$^6$, —C(halogen)$_a$(R$^6_{(2-a)}$)—, —NR$^4$R$^5$—, and —C(O)NR$^4$R$^5$, where R$^4$ and R$^5$ together with the nitrogen to which they are attached form a 5 to 7-membered heterocycle linker;

m is from 0 to 5;

Y is independently selected from the group consisting of: H, $C_1$-$C_{10}$ alkyl, $C_2$-$C_{10}$ alkenyl, $C_2$-$C_{10}$ alkynyl, aryl, $C_3$-$C_{10}$ cycloalkyl, heteroaryl, —OR$^6$, —N(R$^6$)$_2$, —C(O)R$^6$, —C(O)OR$^6$, —C(O)N(R$^6$)$_2$, —SO$_2$—R$^6$, —SO$_2$—N(R$^6$)$_2$, —NH—C(O)—N(R$^6$)$_2$, —NH—SO$_2$—N(R$^6$)$_2$, halogen, —C(halogen)$_b$R$^6_{(3-b)}$, and —NR$^4$R$^5$—C(O)NR$^4$R$^5$, where R$^4$ and R$^5$ together with the nitrogen to which they are attached form a 5- to 7-membered heterocycle;

b is from 1 to 3;

a is 1 or 2;

$R_3$ is a bicyclic heteroaryl containing at least one nitrogen atom; and each R$^6$ is independently selected from the group consisting of H, $C_1$-$C_{10}$ alkyl, aryl or heteroaryl.

13. A pharmaceutical composition comprising a compound according to claim 1, and a pharmaceutically acceptable excipient.

* * * * *